United States Patent
Yamauchi (10) Patent No.: US 11,533,885 B2
(45) Date of Patent: Dec. 27, 2022

(54) **GENUS *NICOTIANA* F1 HYBRID AND USE OF SAME**

(71) Applicant: JAPAN TOBACCO INC., Tokyo (JP)

(72) Inventor: Shun Yamauchi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 105 days.

(21) Appl. No.: 16/926,114

(22) Filed: Jul. 10, 2020

(65) Prior Publication Data

US 2020/0344971 A1 Nov. 5, 2020

Related U.S. Application Data

(63) Continuation of application No. PCT/JP2019/001363, filed on Jan. 10, 2019.

(30) Foreign Application Priority Data

Jan. 11, 2018 (JP) .............................. JP2018-002574

(51) Int. Cl.
  *A01H 6/82* (2018.01)
  *A01H 5/02* (2018.01)
  *A24B 15/10* (2006.01)
  *A24B 15/24* (2006.01)

(52) U.S. Cl.
  CPC .............. *A01H 6/823* (2018.05); *A01H 5/02* (2013.01); *A24B 15/10* (2013.01); *A24B 15/241* (2013.01)

(58) Field of Classification Search
  CPC ........... A01H 6/823; A01H 1/02; A24B 15/10
  See application file for complete search history.

(56) References Cited

U.S. PATENT DOCUMENTS

| 4,153,063 A * | 5/1979 | Roselius ................ A24B 15/24 131/297 |
| 7,798,153 B2 | 9/2010 | Lawrence, Jr. | |
| 2006/0236433 A1* | 10/2006 | Zaitlin ..................... A01H 1/00 530/370 |
| 2019/0218564 A1 | 7/2019 | Suzuki et al. | |

FOREIGN PATENT DOCUMENTS

| CN | 102802451 A | 11/2012 |
| WO | WO 2011/088171 A2 | 7/2011 |
| WO | WO 2017/170796 A1 | 10/2017 |

OTHER PUBLICATIONS

Barbeć A (2015) Nicotiana hybridization map—"blank spots" yet to be filled. In: Coresta Meeting, Agronomy/Phytopathology, 2015, Izmir, Turkey, AP 28 (Year: 2015).*
Ahuja, "A Cytogenetic Study of Heritable Tumors in Nicotiana Species Hybrids," Genetics, vol. 47, Jul. 1962, pp. 865-880.
Bulletin of The Iwata Tobacco Experiment Station, No. 17, Mar. 1985, pp. 1-69.
International Search Report (PCT/ISA/210) issued in PCT/JP2019/001363, dated Apr. 2, 2019.

(Continued)

*Primary Examiner* — Weihua Fan (74) *Attorney, Agent, or Firm* — Birch, Stewart, Kolasch & Birch, LLP (57) ABSTRACT

An object of the present invention is to provide an F1 hybrid or a portion thereof, and use of the F1 hybrid or a portion thereof. The F1 hybrid of the present invention is an F1 hybrid between *Nicotiana umbratica* and *Nicotiana kawakamii*.

31 Claims, 9 Drawing Sheets

| ITEM | F1 HYBRID | *N. umbratica* | *N. kawakamii* |
|---|---|---|---|
| YIELD OF ABOVE-GROUND PART | 1500 G/PLANT | 700 G/PLANT | 2000 G/PLANT |
| NUMBER OF FLOWERS | 130/PLANT | 600/PLANT | 0 TO SEVERAL TENS/PLANT |
| GRASS HEIGHT | 170 cm | 60 cm | 200 cm |
| HEIGHT OF LOWERMOST FLOWER | 110 cm | 7 cm | 180 cm |
| HEIGHT OF LOWERMOST FLOWER/GRASS HEIGHT | 65% | 12% | 90% |
| LEAF LENGTH OF LARGEST LEAF | 60 cm | 20 cm | 60 cm |
| LEAF WIDTH OF LARGEST LEAF | 30 cm | 10 cm | 30 cm |
| NUMBER OF BRANCHES | ABOUT THE SAME AS THE NUMBER OF LEAVES | EXTREMELY LARGE | ABOUT THE SAME AS THE NUMBER OF LEAVES |

(56) References Cited

OTHER PUBLICATIONS

Seibundo Shinkosha Publishing Co., LTD., "The genus *Nicotiana* illustrated," Japan Tobacco Inc., Mar. 1994, pp. 180-183.
Subhashini et al., "Interspecific Hybridization in the Genus *Nicotiana* Involving a New Australian Species *N. umbratica*," Cytologia, vol. 39, 1974, pp. 403-409.
Subhashini, "Interspecific Hybridization in the Genus *Nicotiana* Involving the Species *N. umbratica B* and *N. megalosiphon H* and *M Arg*." Cytologia, vol. 40, 1975, pp. 409-413.
Subhashini. "Study of the Cytoplasmic Effects in the Interspecific Cross Nicotiana Umbratica Burbidge & N. Glutinosa Linn." Euphytica, vol. 23, 1974, pp. 289-293.
Takenaka. "Cytogenetic studies in Nicotiana. XIV. Reduction divisions in five interspecific hybrids," Jap. Jour. Genet., vol. 31, 1956, pp. 155-161.
Written Opinion of the International Searching Authority (PCT/ISA/237) issued in PCT/JP2019/001363, dated Apr. 2, 2019.
Extended European Search Report for European Application No. 19738906.7, dated Oct. 29, 2021.
Gangadev et al., "Morphological and Cytological Studies of Interspecific Hybrids to Nicotiana involving N. umbratica Burbidge," Cytologia, vol. 52, No. 3, 1987, pp. 475-488.
Mizutani et al., "A New Sesquiterpene from Nicotiana umbratica Burbidge," Tetrahedron, vol. 53, No. 34, 1997, pp. 11563-11568.
Mulyadi et al., "Optimization of Nicotine Extraction in Tobacco Leaf (*Nicotiana tabacum* L.) (Study : Comparison of Ether and Petroleum Ether)," The International Conference on Chemical Engineering, 2013, 10 pages total.

\* cited by examiner

Fig. 1

| ITEM | F1 HYBRID | N. umbratica | N. kawakamii |
|---|---|---|---|
| YIELD OF ABOVE-GROUND PART | 1500 G/PLANT | 700 G/PLANT | 2000 G/PLANT |
| NUMBER OF FLOWERS | 130/PLANT | 600/PLANT | 0 TO SEVERAL TENS/PLANT |
| GRASS HEIGHT | 170 cm | 60 cm | 200 cm |
| HEIGHT OF LOWERMOST FLOWER | 110 cm | 7 cm | 180 cm |
| HEIGHT OF LOWERMOST FLOWER/GRASS HEIGHT | 65% | 12% | 90% |
| LEAF LENGTH OF LARGEST LEAF | 60 cm | 20 cm | 60 cm |
| LEAF WIDTH OF LARGEST LEAF | 30 cm | 10 cm | 30 cm |
| NUMBER OF BRANCHES | ABOUT THE SAME AS THE NUMBER OF LEAVES | EXTREMELY LARGE | ABOUT THE SAME AS THE NUMBER OF LEAVES |

Fig. 2

| ITEM | F1 HYBRID | N. umbratica | N. kawakamii |
|---|---|---|---|
| PHOTOGRAPH OF WHOLE PLANT BODY |  |  |  |
| PHOTOGRAPH OF LEAVES |  |  |  |
| PHOTOGRAPHS OF FLOWERS |  |  | |

GENUS *NICOTIANA* F1 HYBRID AND USE OF SAME

CROSS REFERENCE TO RELATED APPLICATIONS

The present application is a continuation application of International Application No. PCT/JP2019/001363, filed on Jan. 10 2019.

TECHNICAL FIELD

The present invention relates to a genus *Nicotiana* F1 hybrid and use thereof.

BACKGROUND ART

1. Plants of Genus *Nicotiana*

Plants of the genus *Nicotiana* (also called "Nicotiana") are widespread in the South/North American Continents, the Australian continent, and also in the African continent, and currently 70 or more species are reported. Two species, *Nicotiana tabacum* and *Nicotiana rustica*, which are each used as a raw material for a tobacco product, are the best known plants of the genus *Nicotiana*.

With respect to wild species of the genus *Nicotiana* other than the two species, there are a large number of reports on genetic analysis and analysis of disease resistance including those using, as a material, a plant obtained by hybridization between wild species. Examples thereof include: Takenaka, Jap. Jour. Genet. 31. 155-161, 1956; and MULKH RAJ AHUJA, Genetica 47, 865-880, 1962. There are reports on utilizing a wild species itself as a raw material for a tobacco product, but the number of such reports is small. Examples thereof include U.S. Pat. No. 7,798,153. However, a report on using an F1 hybrid plant which is obtained by hybridizing wild species for a tobacco product has not been found so far.

2. *Nicotiana umbratica*

"*Nicotiana umbratica*" is a species of the genus *Nicotiana*, spreading in northwestern Western Australia. *Nicotiana umbratica* is an annual grass that has a grass height of about 50 to about 60 cm and grows thick while a large number of thin stems branch, and glandular hairs grow on the whole body to make *Nicotiana umbratica* sticky, and a strong scent floats. The leaf blade of *Nicotiana umbratica* has a wide egg shape having a length of about 8 cm, and *Nicotiana umbratica* has a lot of racemose flowers at the tips of branches with leaves and at the tips of branches at axillary growth. The main alkaloid is nicotine. *Nicotiana umbratica* is resistant to powdery mildew and downy mildew (common) (The genus *Nicotiana* illustrated, Japan Tobacco Inc. (edited), 180-183, 1994 March, SEIBUNDO SHINKOSHA Publishing Co., LTD.). *Nicotiana umbratica* has such a characteristically strong scent and is therefore considered to be preferable as a raw material for a tobacco product. However, a report on utilizing *Nicotiana umbratica* as a raw material for a tobacco product has not been found so far.

On the other hand, genetic analysis and the like using *Nicotiana umbratica* as an experimental material are reported in a large number of literatures. For example, U. Subhashini et al. have reported that hybridization between *Nicotiana umbratica* and another wild species of the genus *Nicotiana* was performed (U. Subushini, Euphytica, 23, 289-293, 1974; U. Subushini at al., Cytologia 39, 403-409, 1974; U. Subushini at al., Cytologia 40, 409-413, 1975).

3. *Nicotiana kawakamii*

*Nicotiana kawakamii* is a species of the genus *Nicotiana*, discovered by Kawakami Yoshiyasu et al. in Bolivia in 1968. In the place of origin, *Nicotiana kawakamii* is a semi-arbor shrub with a height of about 4 m, the stem is sticky, and the tip part is reddish purple. The leaf has an elliptic shape having a length of about 60 cm. The branch having a panicle is thick and spread, has buds and flowers spirally at the tip thereof, and has deep reddish purple capsules in line. The way the leaves grow is dense. The number of flowers is small, and the upper part of the plant body has the flowers together. The main alkaloid is nornicotine. *Nicotiana kawakamii* is resistant to powdery mildew and PVY (The genus *Nicotiana* illustrated, Japan Tobacco Inc. (edited), 180-183, 1994 March, SEIBUNDO SHINKOSHA Publishing Co., LTD.). Utilization for a tobacco product is reported in U.S. Pat. No. 7,798,153 granted to US Smokeless Tobacco Co., but a report on utilizing, for a tobacco product, an F1 hybrid using *Nicotiana kawakamii* as one parent has not been found so far.

CITATION LIST

Patent Literature

PTL 1: U.S. Pat. No. 7,798,153

Non Patent Literature

NPL 1: Takenaka, Jap, Jour. Genet. 31. 155-161, 1956
NPL 2: MULKH RAJ AHUJA, Genetica 47, 865-880, 1962
NPL 3: The genus *Nicotiana* illustrated, Japan Tobacco Inc. (edited), 180-183, 1994 March, SEIBUNDO SHINKOSHA Publishing Co., LTD.
NPL 4: U. Subushini, Euphytica, 23, 289-293, 1974
NPL 5: U. Subushini at al., Cytologia 39, 403-409, 1974
NPL 6: U. Subushini at al., Cytologia 40, 409-413, 1975
NPL 7: BULLETIN OF THE IWATA TOBACCO EXPERIMENT STATION, 17, 1-69, 1985 March

SUMMARY OF INVENTION

Technical Problem

When *Nicotiana umbratica* is utilized as a raw material for a tobacco product, there are major problems such as (i) the plant body is small and the yielding ability is low and (ii) flower buds are formed at every axillary bud/branch, and therefore topping operation (cutting flower buds) which is carried out for inducing maturation of leaves in ordinary cultivation of tobacco is complicated. Means for solving these problems without impairing the properties of *Nicotiana umbratica* s unknown from the information obtained from the literatures.

As one solution, it is supposed to utilize an F1 hybrid which is obtained by hybridizing *Nicotiana umbratica* and another plant of the genus *Nicotiana*, but a problem such that a hybrid seed is not obtained, or germination does not occur even though a hybrid seed is obtained is brought about depending on the combination in hybridization. Further, much labor is needed for picking out a mate satisfying the condition for obtaining an F1 hybrid in which yield ability and complexity in topping operation are ameliorated without impairing a characteristically strong scent of *Nicotiana umbratica*.

An object of the present invention is to provide an F1 hybrid plant in which the yield ability and the complexity in topping operation are ameliorated without impairing the characteristically strong scent of *Nicotiana umbratica*, and a method for making the F1 hybrid plant.

The present inventors have conducted hybridization between *Nicotiana umbratica* and a plurality of wild species of the genus *Nicotiana* and investigated the properties of resultant F1 hybrids in detail to find that an F1 hybrid obtained using a combination of *Nicotiana umbratica* and *Nicotiana kawakamii* has excellent characteristics for obtaining a raw material for a tobacco product, and have thereby reached the present invention.

Solution to Problem

The present invention includes, but not limited to, the following embodiments.

[Embodiment 1] An F1 hybrid between *Nicotiana umbratica* and *Nicotiana kawakamii*, or a portion thereof.

[Embodiment 2] The F1 hybrid or a portion thereof according to embodiment 1, wherein the portion is selected from the group consisting of a leaf, a stem, a root, a seed, a flower, pollen, an anther, an ovule, a pedicel, a meristematic tissue, a seed leaf, an embryonic axis, a pericycle, an embryo, an endosperm, an explant tip, a callus, a tissue-cultured product, a bud, a cell, and a protoplast.

[Embodiment 3] The F1 hybrid or a portion thereof according to embodiment 1 or 2, wherein a seed parent is *Nicotiana umbratica*, and a pollen parent is *Nicotiana kawakamii*.

[Embodiment 4] The F1 hybrid or a portion thereof according to embodiment 1 or 2, wherein a pollen parent is *Nicotiana umbratica*, and a seed parent is *Nicotiana kawakamii*.

[Embodiment 5] The F1 hybrid or a portion thereof according to any one of embodiments 1 to 4, wherein a ratio (%) of height of a lowermost flower to grass height increases as compared to *Nicotiana umbratica*.

[Embodiment 6] The F1 hybrid or a portion thereof according to any one of embodiments 1 to 5, wherein a number of flowers per plant is smaller than that of *Nicotiana umbratica*.

[Embodiment 7] The F1 hybrid or a portion thereof according to any one of embodiments 1 to 6, wherein a leaf length or a leaf width of a largest leaf is longer than that of *Nicotiana umbratica*, or both of a leaf length and a leaf width of a largest leaf are longer than those of *Nicotiana umbratica*.

[Embodiment 8] The F1 hybrid or a portion thereof according to any one of embodiments 1 to 7, wherein a number of branches is decreased as compared to the number of branches of *Nicotiana umbratica*.

[Embodiment 9] The F1 hybrid or a portion thereof according to any one of embodiments 1 to 8, wherein a yield of an above-ground part increases as compared to *Nicotiana umbratica*.

[Embodiment 10] The F1 hybrid or a portion thereof according to any one of embodiments 1 to 9, wherein a yield of dried leaves increases as compared to *Nicotiana umbratica*.

[Embodiment 11] The F1 hybrid or a portion thereof according to any one of embodiments 1 to 10, wherein insect resistance against a defoliator pest is improved as compared to *Nicotiana kawakamii*.

[Embodiment 12] The F1 hybrid or a portion thereof according to any one of embodiments 1 to 11, wherein insect resistance against a defoliator pest is improved as compared to both of *Nicotiana kawakamii* and *Nicotiana umbratica*.

[Embodiment 13] The F1 hybrid or a portion thereof according to any one of embodiments 1 to 12, wherein insect resistance against a stored-tobacco pest is improved as compared to *Nicotiana kawakamii*.

[Embodiment 14] The F1 hybrid or a portion thereof according to any one of embodiments 1 to 13, wherein insect resistance against a stored-tobacco pest is improved as compared to both of *Nicotiana kawakamii* and *Nicotiana umbratica*.

[Embodiment 15] The F1 hybrid or a portion thereof according to embodiment 11 or 12, wherein the defoliator pest is selected from the group consisting of oriental tobacco budworm (*Helicoverpa assulta*), tobacco budworm (*Heliothis virescens*), cotton bollworm (*Helicoverpa armigera*), tobacco hornworm (*Manduca sexta*), *Spodoptera litura*, and *Spodoptera exigua*.

[Embodiment 16] A method for making an F1 hybrid, comprising hybridizing *Nicotiana umbratica* and *Nicotiana Kawakamii*.

[Embodiment 17] The method according to embodiment 16, wherein a seed parent is *Nicotiana umbratica*, and a pollen parent is *Nicotiana kawakamii*.

[Embodiment 18] The method according to embodiment 16, wherein a pollen parent is *Nicotiana umbratica*, and a seed parent is *Nicotiana kawakamii*.

[Embodiment 19] The method according to any one of embodiments 16 to 18, further comprising a step of choosing the F1 hybrid having a ratio (%) of a height of a lowermost flower to a grass height increased as compared to *Nicotiana umbratica* after hybridizing *Nicotiana umbratica* and *Nicotiana Kawakamii*.

[Embodiment 20] The method according to any one of embodiments 16 to 18, further comprising a step of choosing the F1 hybrid having a number of flowers per plant smaller than the number of flowers of *Nicotiana umbratica* after hybridizing *Nicotiana umbratica* and *Nicotiana Kawakamii*.

[Embodiment 21] The method according to any one of embodiments 16 to 18, further comprising a step of choosing the F1 hybrid having a longer leaf length or a leaf width of a largest leaf, or both of a longer leaf length and a leaf width of a largest leaf than *Nicotiana umbratica* after hybridizing *Nicotiana umbratica* and *Nicotiana kawakamii*.

[Embodiment 22] The method according to any one of embodiments 16 to 18, further comprising a step of choosing the F1 hybrid having a number of branches decreased as compared to *Nicotiana umbratica* after hybridizing *Nicotiana umbratica* and *Nicotiana Kawakamii*.

[Embodiment 23] The method according to any one of embodiments 16 to 18, further comprising a step of choosing the F1 hybrid having a yield of an above-ground part increased as compared to *Nicotiana umbratica* after hybridizing *Nicotiana umbratica* and *Nicotiana Kawakamii*.

[Embodiment 24] The method according to any one of embodiments 16 to 18, further comprising a step of choosing the F1 hybrid having a yield of dried leaves increased as compared to *Nicotiana umbratica* after hybridizing *Nicotiana umbratica* and *Nicotiana Kawakamii*.

[Embodiment 25] A composition comprising the F1 hybrid or a portion thereof according to any one of embodiments 1 to 15, or a composition comprising an extract of the F1 hybrid or a portion thereof according to any one of embodiments 1 to 15.

[Embodiment 26] The composition according to embodiment 25, being in a cut filler, powder, sheet, or solution form.

[Embodiment 27] A product comprising the F1 hybrid or a portion thereof according to any one of embodiments 1 to 15, or a product comprising an extract of the F1 hybrid or a portion thereof according to any one of embodiments 1 to 15.

[Embodiment 28] A product comprising the composition according to embodiment 25 or embodiment 26.

[Embodiment 29] The product according to embodiment 27 or 28, selected from the group consisting of a tobacco product, a perfume, an agricultural chemical, and a pharmaceutical product.

[Embodiment 30] Use of the F1 hybrid or a portion thereof according to any one of embodiments 1 to 15, or a use of an extract of the F1 hybrid or a portion thereof according to any one of embodiments 1 to 15 for producing a composition or a product.

Advantageous Effects of Invention

An F1 hybrid obtained by hybridizing *Nicotiana umbratica* and *Nicotiana kawakamii* is an F1 hybrid in which the yield increases and the easiness of removing the flower part is improved as compared to *Nicotiana umbratica* without impairing the characteristic scent of *Nicotiana umbratica*. Special technique/know-how are unnecessary for cultivation management of the F1 hybrid, and the F1 hybrid can easily be cultivated until harvest by almost the same management as in general *Nicotiana tabacum*.

The problems of conventional techniques can remarkably be ameliorated by making an F1 hybrid between wild species using *Nicotiana umbratica* and *Nicotiana kawakamii* and utilizing the F1 hybrid that improves the yield and the easiness of removing the flower part without impairing the characteristic scent of *Nicotiana umbratica*. The F1 hybrid further has an effect of enabling remarkable suppression of the extent of being eaten by insects in *Nicotiana umbratica*.

DESCRIPTION OF EMBODIMENTS

The present invention includes, but not limited to, the following embodiments.

1. F1 Hybrid

The present invention relates to an F1 hybrid between *Nicotiana umbratica* and *Nicotiana kawakamii*, or a portion thereof.

"*Nicotiana umbratica*" is a species of the genus *Nicotiana*, spreading in northwestern Western Australia. The chromosome number (2n) is 46. *Nicotiana umbratica* has a grass height of about 50 to about 60 cm, grows thick while a large number of thin stems branch, and has a large number of small leaves of about 5 to about 15 cm, although not limited thereto. *Nicotiana umbratica* has a lot of racemose flowers at the tips of branches. *Nicotiana umbratica* as the whole plant body has a large secretion quantity from trichomes to be sticky, and a strong scent floats from the whole, although not limited thereto. The main alkaloid component is nicotine.

*Nicotiana kawakamii* is a species discovered by Kawakami Yoshiyasu et al. in Bolivia in 1968. The chromosome number (2n) is 24. The grass height of *Nicotiana kawakamii* becomes 200 cm or more in average, and the leaf is large, although not limited thereto. The main alkaloid component is nornicotine.

The "F1 hybrid" is progeny born from plants whose species or varieties are different. The "F1 hybrid" in the present specification and the claims of the present application means an F1 hybrid as the first filial generation (F1). F1 is the first generation progeny generated as a result of hybridization between parents having certain different alleles as being homozygous in a living thing. F1 has genes of the parents as being heterozygous, and the genotype is uniform. The chromosome number (2n) is 35.

The portion of the F1 hybrid in the present invention includes not only a portion of an adult of a plant but also all the embodiments from a seed to an adult of a plant.

The "portion" is selected from the group consisting of a leaf (including a leaf blade and a leafstalk), a stem, a root, a seed, a flower, pollen, an anther, an ovule, a pedicel, a meristematic tissue, a seed leaf, an embryonic axis, a pericycle, an embryo, an endosperm, an explant tip, a callus, a tissue-cultured product, a bud, a cell, and a protoplast, although not limited thereto. The portion is preferably a leaf or a stem.

The "leafstalk" is a small shaft that connects a leaf blade and a stem in a plant. The "pedicel" is a short shaft that joins a single-petaled flower and a stem which leads to inflorescence in a seed plant. The "pericycle" is a tissue of a plant and is a layer of cells, the layer surrounding a xylem where the center of a root exists and a phloem. When the pericycle divides, a lateral root is thereby formed. The "explant tip" is a tissue slice of a plant, the tissue slice obtained by culturing under an artificial condition a portion of an embryo cut out from the plant. The "callus" is a lump of undifferentiated plant cells which are being cultured on a solid medium or the like. The "tissue-cultured product" is a cultured product of a plant tissue obtained by culturing an arbitrary tissue of a plant under an artificial condition.

In the F1 hybrid, any of *Nicotiana umbratica* and *Nicotiana kawakamii* may be a seed parent or may be a pollen parent.

In one embodiment, the seed parent is *Nicotiana umbratica*, and the pollen parent is *Nicotiana kawakamii*. In another embodiment, the pollen parent is *Nicotiana umbratica*, and the seed parent is *Nicotiana kawakamii*. More preferably, the seed parent is *Nicotiana umbratica*, and the pollen parent is *Nicotiana kawakamii*.

2. Characteristics of F1 Hybrid (1) Easiness of Removal of Flowers

To efficiently collect the above-ground part including leaves and stems each useful in order to be used for producing a tobacco product from a tobacco plant, it is necessary to remove the flowers from the tobacco plant. Removal of flowers are easier in the F1 hybrid than in *Nicotiana umbratica*.

In one embodiment, the ratio (%) of the height of a lowermost flower to the grass height increases as compared to *Nicotiana umbratica*. The ratio (%) of the height of a lowermost flower to the grass height is preferably 20% or more, 30% or more, 40% or more, 50% or more, 60% or more, or 65% or more. In one embodiment, the ratio (%) of the height of a lowermost flower to the grass height is 40% or more.

In one embodiment, the number of flowers per plant is smaller in the F1 hybrid than that of *Nicotiana umbratica*. In Example 1, which will be described later, the "number of flowers" per plant about 50 days after transplantation decreased in the F1 hybrid to about one fifth of that in *Nicotiana umbratica*. The number of flowers per plant in the F1 hybrid is preferably two thirds or less, one half or less, one third or less, one fourth or less, or one fifth or less of that in *Nicotiana umbratica*.

In the F1 hybrid, the number of flowers is small, and the flowers are localized at the upper part, and therefore removal of the flowers is easy.

(2) Harvest of Above-Ground Part

The above-ground part including leaves and stems each useful in order to be used for producing a tobacco product can preferably be harvested more in the F1 hybrid than in *Nicotiana umbratica*.

In one embodiment, the yield of the above-ground part increases in the F1 hybrid as compared to *Nicotiana umbratica*.

The yield of the above-ground part per plant is preferably 1.2 times or more, 1.5 times or more, 1.8 times or more, 2 times or more, or 2.1 times or more as compared to *Nicotiana umbratica*.

In one embodiment, the yield of dried leaves increases in the F1 hybrid as compared to *Nicotiana umbratica*. The "dried leaves" are leaves obtained by subjecting the leaves of a tobacco plant to a drying treatment, such as freeze drying, drying by heating, drying in the sun, or air drying, thereby drying the leaves of the tobacco plant.

In one embodiment, the leaf length or leaf width of the largest leaf in the F1 hybrid is longer than that of *Nicotiana umbratica*, or both of the leaf length and leaf width of the largest leaf in the F1 hybrid are longer than those of *Nicotiana umbratica*. In Example 1, the leaf length and leaf width of the largest leaf in the F1 hybrid were about 3 times those of *Nicotiana umbratica* at 90 days after transportation. Accordingly, the leaf length or leaf width of the largest leaf, or both of the leaf length and leaf width of the largest leaf in the F1 hybrid are preferably 1.5 times, 2 times, 2.5 times, or 3 times those of *Nicotiana umbratica*.

In one embodiment, the number of branches decreases in the F1 hybrid as compared to *Nicotiana umbratica*. In one embodiment, the "number of branches" is about the same as the number of leaves. Harvest of leaves is easier than for *Nicotiana umbratica*. In addition, in one embodiment, the extent of growth of axillary buds is lower than that of *Nicotiana umbratica*. Accordingly, harvest of leaves is easy in the F1 hybrid.

In a preferred embodiment, the yield of the above-ground part is larger, and in addition, harvest of leaves is easier in the F1 hybrid as compared to *Nicotiana umbratica*.

(3) Insect Resistance Against Pest

The F1 hybrid preferably has strong resistance against a pest.

It is generally known that *Nicotiana kawakamii* which is a wild species has weak insect resistance against a lot of pests, and *Nicotiana umbratica* has strong insect resistance against a pest.

In one embodiment, the insect resistance against a defoliator pest is improved in the F1 hybrid as compared to *Nicotiana kawakamii*. More preferably, the insect resistance against a defoliator pest is improved in the F1 hybrid as compared to both of *Nicotiana kawakamii* and *Nicotiana umbratica*.

In one embodiment, the insect resistance against a stored-product pest is improved in the F1 hybrid as compared to *Nicotiana kawakamii*. More preferably, the insect resistance against a stored-product pest is improved in the F1 hybrid as compared to both of *Nicotiana kawakamii* and *Nicotiana umbratica*.

In one embodiment, the insect resistance against a defoliator pest is improved in the F1 hybrid as compared to *Nicotiana tabacum*.

In one embodiment, the insect resistance against a stored-product pest is improved in the F1 hybrid as compared to *Nicotiana tabacum*.

In the present specification and the appended Claims, the "pest" is used as a general term of an arbitrary insect that is harmful to a tobacco plant. Examples of the defoliator pest include oriental tobacco budworm (*Helicoverpa assulta*), tobacco budworm (*Heliothis virescens*), cotton bollworm (*Helicoverpa armigera*), tobacco hornworm (*Manduca sexta*), *Spodoptera litura*, and *Spodoptera exigua*.

Oriental tobacco budworm (*Helicoverpa assulta*) the larva (green caterpillar) of which in particular eats various farm products is particularly known as a pest against solanaceous plants, such as tobacco and a sweet pepper, fruits, flowers, and the like. The "green caterpillar" is a green larva the body of which is not covered with long hair among the larvae of Lepidoptera (butterflies and moths).

Examples of the stored-product pest include pests that eat dried leaves of tobacco, such as Lasioderma serricorne and Ephestia elutella.

(4) Components Contained in Tobacco

Preferably, all or part of components that contribute to the characteristic flavor (preferred flavor as tobacco) does not decrease in the F1 hybrid as compared to *Nicotiana umbratica*. Examples of the components that contribute to the preferred scent as tobacco include 1-isopropyl-5-(hydroxymethyl)-8-methyltricyclo[4.4.0.02,8]dec-4-ene, 3-methylvaleric acid, and 4-methylhexanoic acid.

Accordingly, the F1 hybrid can be used for a product, such as a tobacco product or a perfume, while retaining the preferred flavor of *Nicotiana umbratica*.

3. Method for Making F1 Hybrid

The present invention provides a method for making an F1 hybrid in one embodiment. The method of the present invention includes hybridizing *Nicotiana umbratica* and *Nicotiana kawakamii*. A known method for hybridizing tobacco plants can be used for the hybridization.

In the method for making an F1 hybrid of the present invention, any of *Nicotiana umbratica* and *Nicotiana kawakamii* may be a seed parent or may be a pollen parent.

In one embodiment, the seed parent is *Nicotiana umbratica*, and the pollen parent is *Nicotiana kawakamii*. In another embodiment, the pollen parent is *Nicotiana umbratica*, and the seed parent is *Nicotiana kawakamii*. More preferably, the seed parent is *Nicotiana umbratica*, and the pollen parent is *Nicotiana kawakamii*.

In one embodiment of the method for making an F1 hybrid of the present invention, a step of choosing the F1 hybrid having a more preferred characteristic may be included after hybridizing *Nicotiana umbratica* and *Nicotiana kawakamii*. The step of choosing the F1 hybrid can be performed based on the characteristics, such as the ratio (%) of the height of a lowermost flower to the grass height, the number of flowers per plant, the leave length or leave width of the largest leaf, or both of the leave length and the leave width of the largest leaf, the number of branches, the yield of the above-ground part, and the yield of dried leaves, although not limited thereto. These characteristics are as described in "2. Characteristics of F1 Hybrid". The step of choosing the F1 hybrid may be performed by combining a plurality of choosing steps in terms of a plurality of characteristics given above as examples. The order in the case of performing a plurality of choosing steps is not particularly limited.

4. Composition

The present invention provides a composition containing the F1 hybrid or a portion thereof, or a composition containing an extract of the F1 hybrid or a portion thereof in one embodiment.

With respect to the composition, all or a portion of a tobacco plant may be used as it is, or all or a portion of a tobacco plant cut, pulverized, or ground into a slender piece-like, slurry-like, or fine particle-like product may be used. With respect to the composition, all or a portion of a tobacco plant body harvested from farmland or the like may be used as it is, all or a portion of a tobacco plant body obtained by being left to stand indoors or outdoors for a predetermined period of time to dissipate part of moisture may be used, or all or a portion of a tobacco plant body obtained by almost dissipating moisture with a drier or the like may be used.

The "extract" is obtained by subjecting a tobacco plant-derived material, such as leaves or stems, to extraction for the purpose of ameliorating the flavor of a tobacco product or for the purpose of lowering the contents of particular components in a tobacco product. As an extraction method, a known method for extracting refined oil, a particular component, or the like from a plant can be used.

The composition is in a cut filler, powder, sheet, or solution form, although not limited thereto.

5. Product

The above described F1 hybrid or a portion thereof, or an extract of the F1 hybrid or a portion thereof, and the composition containing the F1 hybrid or a portion thereof or the composition containing an extract of the F1 hybrid or a portion thereof have characteristic flavor derived from *Nicotiana umbratica*. Accordingly, in one embodiment, the characteristic flavor derived from *Nicotiana umbratica* can be imparted to a product by using any of these as a raw material for a tobacco product or the like.

The present invention provides a product including the above-described F1 hybrid or a portion thereof, or a product including an extract of the above-described F1 hybrid or a portion thereof in one embodiment.

The present invention provides a product including a composition containing the above-described F1 hybrid or a portion thereof, or a product including a composition containing an extract of the above-described F1 hybrid or a portion thereof in one embodiment. The product includes, but not limited to, a tobacco product, a perfume, an agricultural chemical, and a pharmaceutical product.

The type of the "tobacco product" is not particularly limited. In addition to a cigarette, a cigar, a pipe tobacco, snuff, a chewing tobacco, a finely shredded tobacco, a water pipe, and the like are included. Further, a heating type flavor inhaler using, as an aerosol source, aerosol which is generated by heating tobacco, a non-heating type flavor inhaler for inhaling the flavor of tobacco without heating the tobacco, and the like are also included.

The types of the perfume and the agricultural chemical are not limited, too. Examples of the agricultural chemical include agricultural chemicals intended for control of a germ, a nematode, a tick, an insect, a mouse, and other animals and plants, or a virus that harms "farm products", and promotion or inhibition of physiological functions, or inhibition of germination of farm products and the like. The perfume, agricultural chemical, and pharmaceutical product can be used singly or together with another active ingredient.

The present invention provides use of the F1 hybrid or a portion thereof, or an extract of the F1 hybrid or a portion thereof for producing a composition or a product in one embodiment.

EXAMPLES

Hereinafter, the present invention will be described in detail based on Examples, but the present invention is not limited to these Examples. A person skilled in the art can easily modify/change the present invention based on the description of the present specification, and such modifications and changes are included in the technical scope of the present invention.

Example 1 Making F1 Hybrid Between *Nicotiana umbratica* and *Nicotiana kawakamii*

In the present Example, an F1 hybrid between *Nicotiana umbratica* and *Nicotiana kawakamii* was made.

Hybridization was performed by a known method using *Nicotiana umbratica* (obtained from Dr. E. L. Moore of United States of America in 1967) as a seed parent and *Nicotiana kawakamii* (obtained from the Central Andes academic investigation team of Kyoto University in 1976) as a pollen parent. The objective F1 hybrid was also obtained when the seed parent and the pollen parent were replaced with each other. Hereinafter, in the present Example, detailed description will be made taking the case where *Nicotiana umbratica* was used as a seed parent, and *Nicotiana kawakamii* was used as a pollen parent as an example.

The obtained F1 hybrid between *Nicotiana umbratica* and *Nicotiana kawakamii* was cultivated (compost: 100 kg/10 a, compound fertilizer (Agri 622): 100 kg/10 a (6 kgN/10 a), superphosphate of lime: 80 kg/10 a, and plant and wood ash: 30 kg/10 a) in a rainfall interception field of JT Leaf Tobacco Research Center (Oyama-shi, Tochigi). The field was covered with Iwatani Reverse Multi Silver Black Type (obtained n from Iwatani Material Corp. (Chuo-ward, Tokyo)) after ridging, the F1 hybrids were transplanted at intervals between plants of 40 cm, and water was sprinkled with a watering tube about 5 times during the whole period. As Comparative Examples, *Nicotiana umbratica* and *Nicotiana kawakamii* were also cultivated in the same manner.

Figure 1:
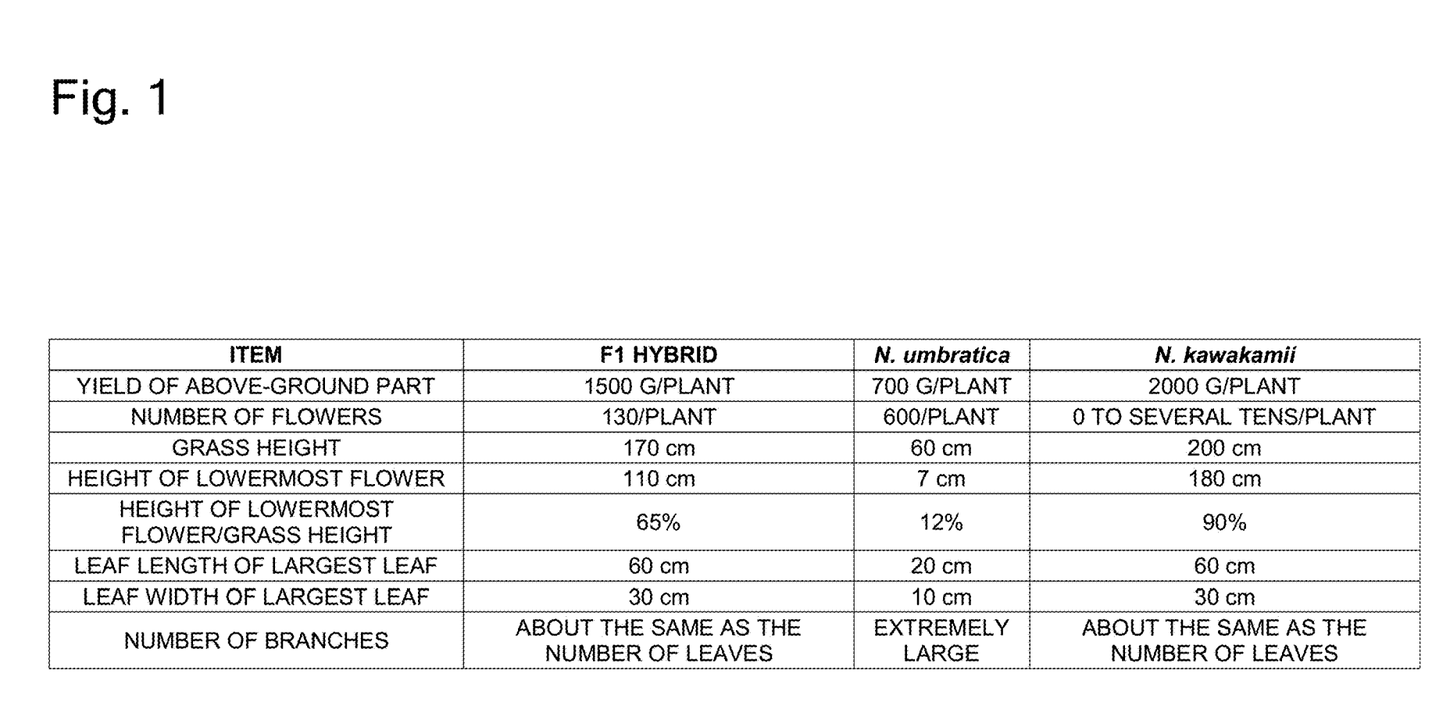
FIG. 1 shows comparative evaluation of characteristics of an F1 hybrid tobacco plant (F1 hybrid) between *Nicotiana umbratica* and *Nicotiana kawakamii*, *Nicotiana umbratica*, and *Nicotiana kawakamii*.
Figure 2:
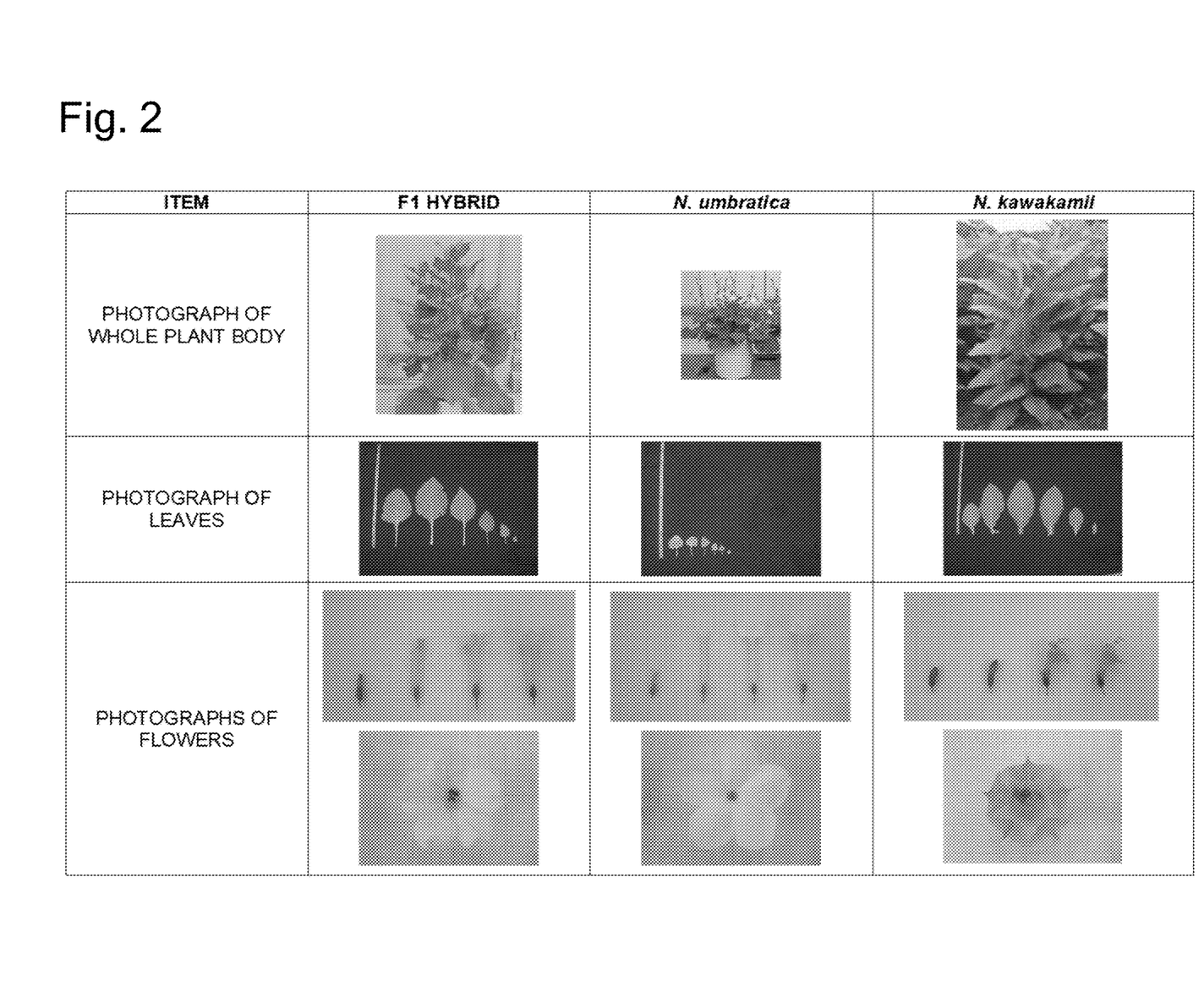
FIG. 2 shows a photograph of the whole plant body, a photograph of leaves, and photographs of flowers of an F1 hybrid, *Nicotiana umbratica*, and *Nicotiana kawakamii*.

Five plants were cultivated for each of the F1 hybrid, *Nicotiana umbratica*, and *Nicotiana kawakamii* to evaluate each item in FIG. 1 and FIG. 2. The items are each shown as an average value for each of the F1 hybrid, *Nicotiana umbratica*, and *Nicotiana kawakamii* unless otherwise noticed. The items were each evaluated about 90 days after seeding unless otherwise noticed.

The insect resistance against a defoliator pest was evaluated in such a way that insects were scattered in a mesh cage in which tobacco leaves were arranged, and the areas of the leaves left after one day were compared.

(1) Yield (Weight of Above-Ground Part Before Drying)

Figure 3:
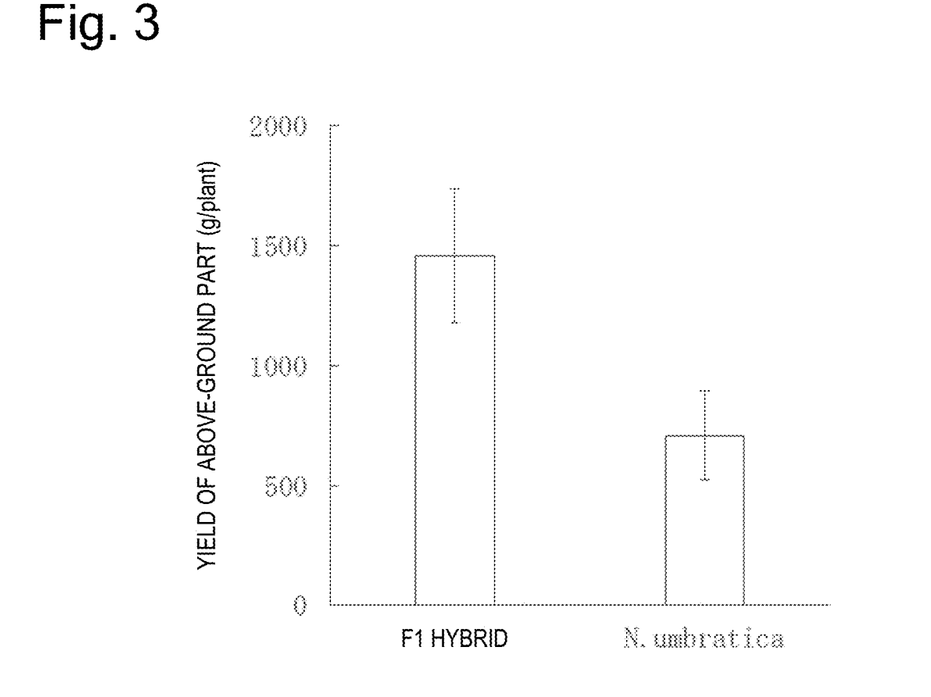
FIG. 3 is a bar graph showing a yield of an above-ground part of an F1 hybrid and *Nicotiana umbratica*.

The yield of each plant of the F1 hybrid, *Nicotiana umbratica*, and *Nicotiana kawakamii* in FIG. 1 was shown in a bar graph of FIG. 3. The "yield of the above-ground part" means the weight of an above-ground part before drying, the above-ground part cut and separated from an individual at a position about 3 cm above the ground 50 days after transplantation. It is to be noted that the flower part in this case is removed with some stem parts. The yield of the above-ground part per plant of the F1 hybrid was about 2 times that of *Nicotiana umbratica*.

(2) Easiness of Removal of Flowers and Easiness of Harvest of Leaves

Figure 4:
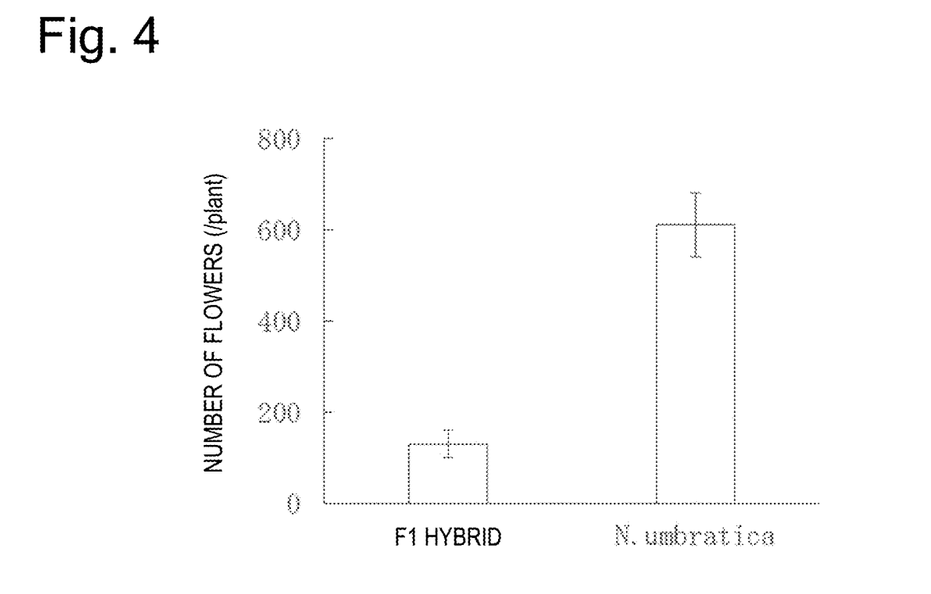
FIG. 4 is a bar graph showing a number of flowers of an F1 hybrid and *Nicotiana umbratica*.
Figure 5:
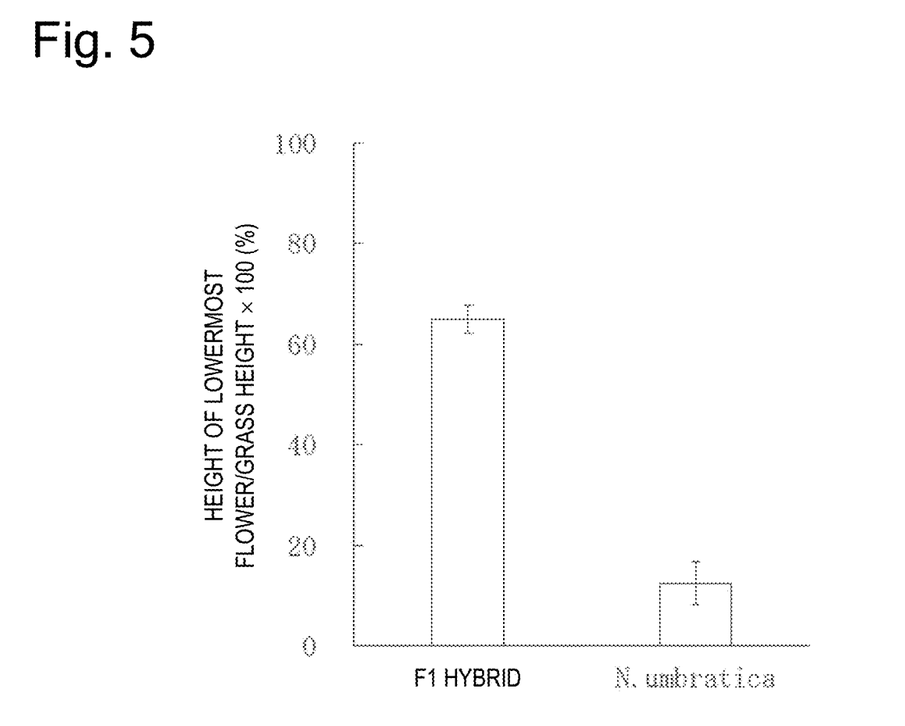
FIG. 5 is a bar graph showing a ratio (%) of a height of a lowermost flower to a grass height of an F1 hybrid and *Nicotiana umbratica*.

As it is understood from the "grass height" in FIG. 1 and the photographs of the whole plant bodies in FIG. 2, the grass height is longer than that of the F1 hybrid and of *Nicotiana umbratica*. The "number of flowers" about 50 days after transplantation is shown in the bar graph of FIG. 4. The number of flowers per plant of the F1 hybrid remarkably decreased to about ⅕ of that of *Nicotiana umbratica*. The ratio (%) of the height of a lowermost flower to the grass height is shown in the bar graph of FIG. 5. In *Nicotiana umbratica*, the flowers were widely distributed from the lower part which is lower than about 20% of the grass height to the upper part, but in the F1 hybrid, the flowers were localized only in the upper part which is higher than about 60% of the grass height in the F1 hybrid. As shown in the "number of flowers", "height of lowermost flower" and "height of lowermost flower/grass height" in FIG. 1, and in FIG. 4 and FIG. 5, the number of flowers is smaller, and the flowers are localized at the upper part, and therefore removal of the flowers is easier in the F1 hybrid of the present invention as compared to *Nicotiana umbratica*.

Further, the number of branches was also smaller than that of *Nicotiana umbratica* and was about the same as the number of leaves, and the extent of growth of axillary buds was lower than that of *Nicotiana umbratica*. Accordingly, harvest of leaves is easier in the F1 hybrid of the present invention than in *Nicotiana umbratica*.

Example 2 Insect Resistance of F1 Hybrid Between *Nicotiana umbratica* and *Nicotiana kawakamii* Against Defoliator Pest In the present Example, the insect resistance of the F1 hybrid between *Nicotiana umbratica* and *Nicotiana kawakamii* of the present invention against feeding damage by oriental tobacco budworm (*Helicoverpa assulta*) was investigated. Young leaves of respective plants described in the following Examples 2-1 to 2-4 were placed in a net cage of 40 cm in width×40 cm in depth×40 cm in height together with 20 to 30 larvae of oriental tobacco budworm (*Helicoverpa assulta*), and the area of the leaves left after one day was compared to that before starting the investigation to investigate variety selectivity of eating. The investigation was carried out in a room with a window out of direct sunlight in the JT Leaf Tobacco Research Center (Oyama-shi, Tochigi Japan) in July 2017, and the room temperature was set to about 25° C. In Examples 2-1 to 2-4, the number and arrangement of varieties which were used as Comparative Examples were changed in order to eliminate (minimize) the influence of the type, arrangement, and the like in Comparative Examples on the variety selectivity of eating.

(1) Example 2-1

In Example 2-1, three types of leaves of *Nicotiana umbratica, Nicotiana kawakamii*, and *Nicotiana tabacum*

Figure 6:
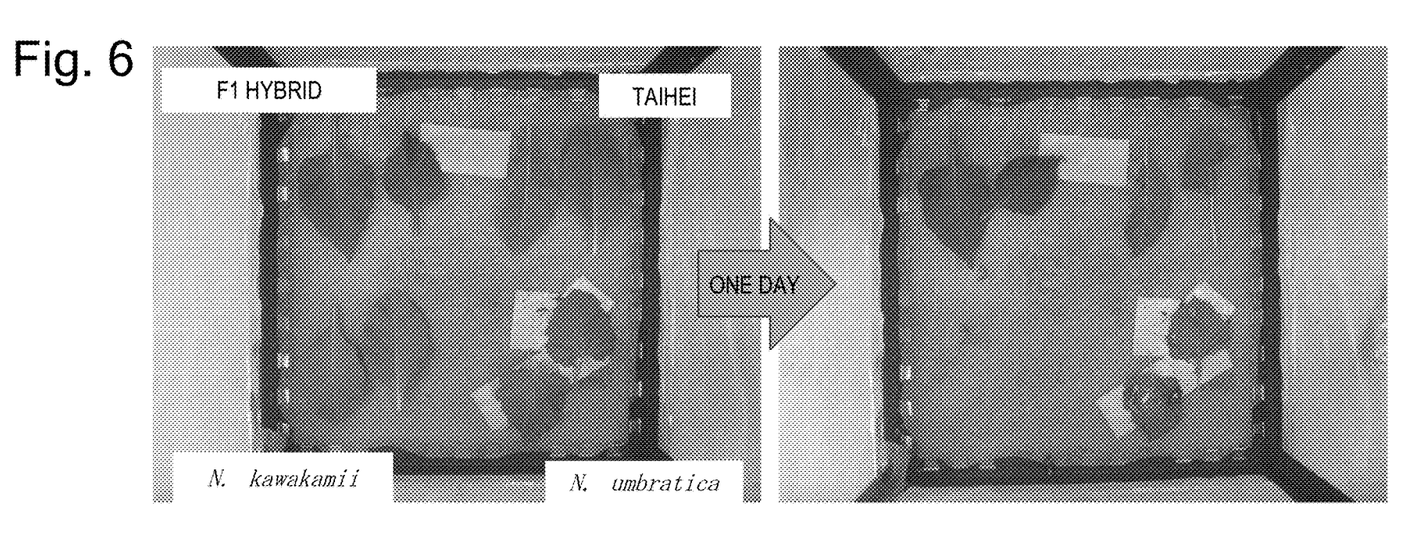
FIG. 6 includes a photograph (left) showing an arrangement of leaves of each plant of an F1 hybrid, *Nicotiana umbratica*, *Nicotiana kawakamii*, and *Nicotiana tabacum* (variety: taihei), and a photograph (right) showing a state one day after larvae of oriental tobacco budworm (*Helicoverpa assulta*) are placed in an investigation on insect resistance against larvae of oriental tobacco budworm (*Helicoverpa assulta*) in Example 2-1.
Figure 7:
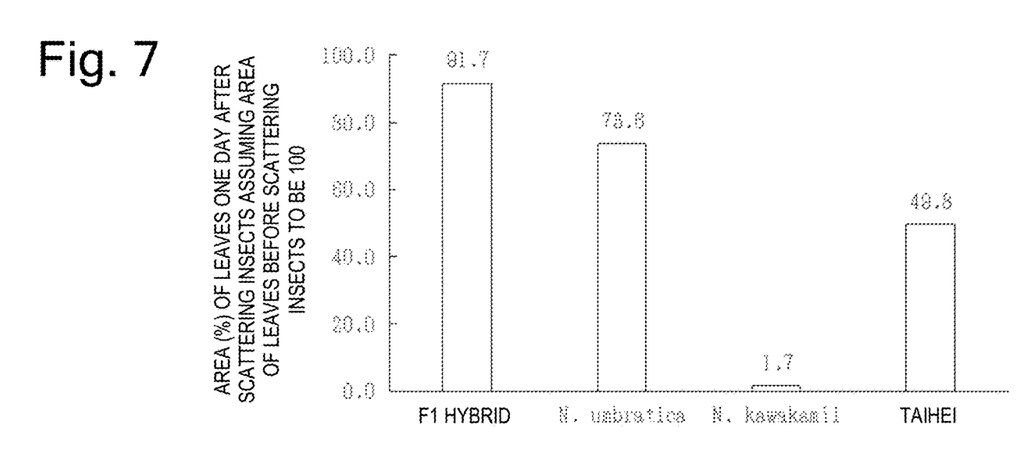
FIG. 7 is a bar graph showing a ratio (%) of an area of leaves after scattering insects to an area of leaves before scattering insects in Example 2-1.

(variety: taihei) as Comparative Examples in addition to the F1 hybrid were arranged as shown in FIG. 6. The area (%) of leaves one day after scattering the insects assuming the area of leaves before scattering the insects to be 100 is shown in FIG. 7. The larvae of oriental tobacco budworm (*Helicoverpa assulta*) ate the leaves of respective plants selectively. That is, the leaves of *Nicotiana kawakamii* were eaten up almost completely, but 70% or more of the leaves were left in *Nicotiana umbratica*, and the F1 hybrid was almost in an undamaged state even after one day. About 50% of the leaves were left in *Nicotiana tabacum* (variety: taihei).

(2) Example 2-2

Figure 8:
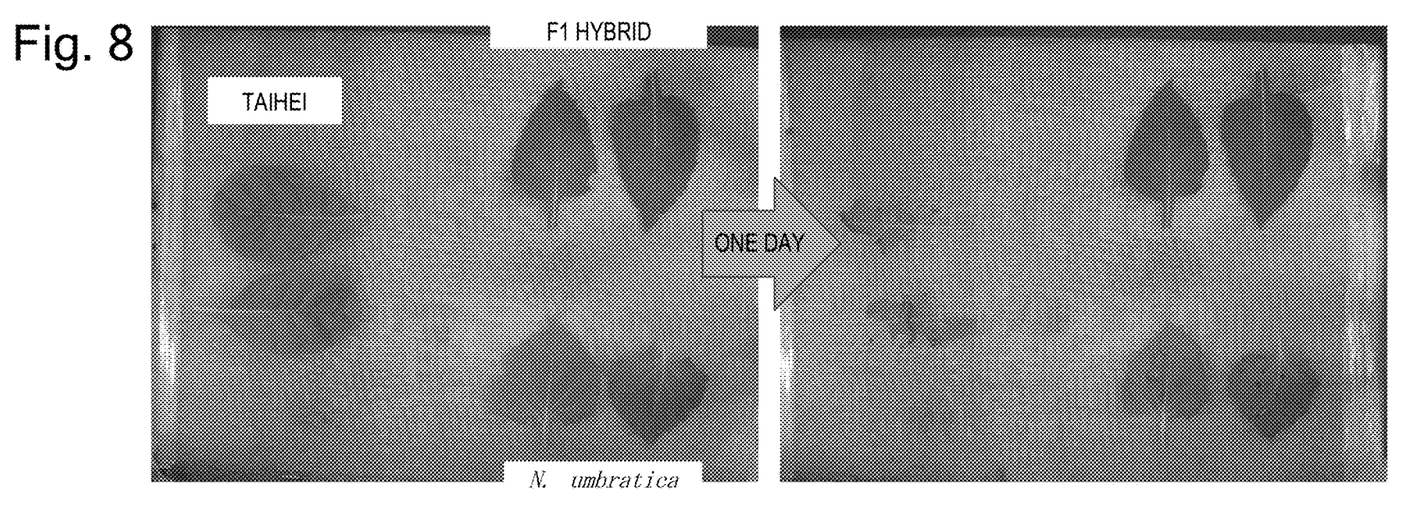
FIG. 8 includes a photograph (left) showing an arrangement of leaves of each plant of an F1 hybrid, *Nicotiana umbratica*, and *Nicotiana tabacum* (variety: taihei), and a photograph (right) showing a state one day after larvae of oriental tobacco budworm (*Helicoverpa assulta*) are placed in an investigation on insect resistance against larvae of oriental tobacco budworm (*Helicoverpa assulta*) in Example 2-2.
Figure 9:
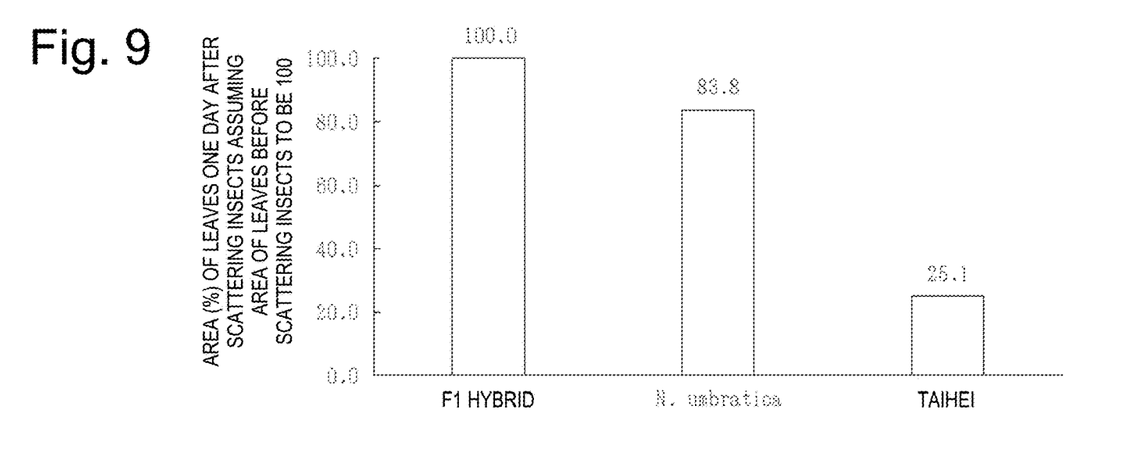
FIG. 9 is a bar graph showing a ratio (%) of an area of leaves after scattering insects to an area of leaves before scattering insects in Example 2-2.

In Example 2-2, two types of leaves of *Nicotiana umbratica* and *Nicotiana tabacum* (variety: taihei) as Comparative Examples in addition to the F1 hybrid were arranged as shown in FIG. 8. The area (%) of leaves one day after scattering the insects assuming the area of leaves before scattering the insects to be 100 is shown in FIG. 9. The larvae of oriental tobacco budworm (*Helicoverpa assulta*) ate the leaves of respective plants selectively. That is, about 80% of the leaves of Taihei were eaten, but less than 20% of the leaves were eaten and 80% or more of the leaves were left in *Nicotiana umbratica*, and the F1 hybrid was almost in an undamaged state even after one day.

(3) Example 2-3

Figure 10:
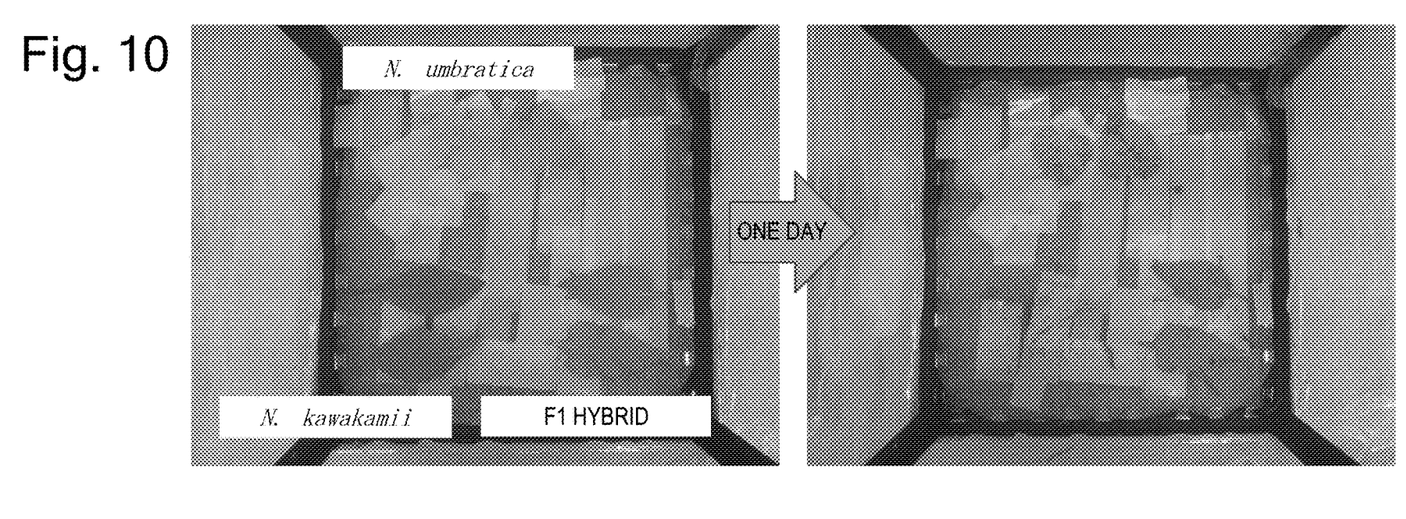
FIG. 10 includes a photograph (left) showing an arrangement of leaves of each plant of an F1 hybrid, *Nicotiana umbratica*, and *Nicotiana kawakamii*, and a photograph (right) showing a state one day after larvae of oriental tobacco budworm (*Helicoverpa assulta*) are placed in an investigation on insect resistance against larvae of oriental tobacco budworm (*Helicoverpa assulta*) in Example 2-3.
Figure 11:
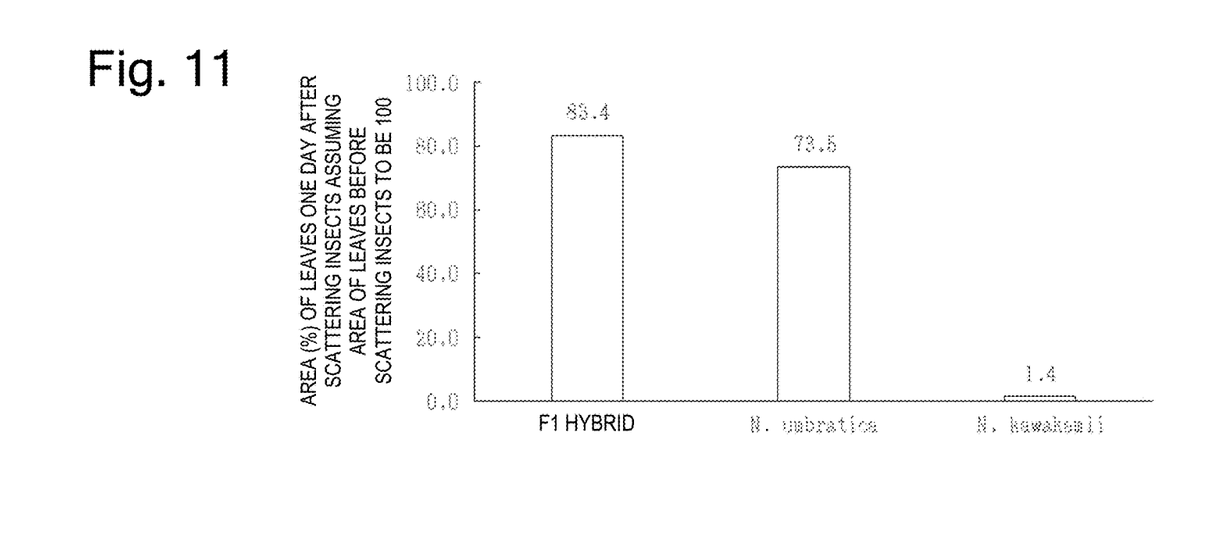
FIG. 11 is a bar graph showing a ratio (%) of an area of leaves after scattering insects to an area of leaves before scattering insects in Example 2-3.

In Example 2-3, two types of leaves of *Nicotiana umbratica* and *Nicotiana kawakamii* as Comparative Examples in addition to the F1 hybrid were arranged as shown in FIG. 10. The area (%) of leaves one day after scattering the insects assuming the area of leaves before scattering the insects to be 100 is shown in FIG. 11. The larvae of oriental tobacco budworm (*Helicoverpa assulta*) ate the leaves of respective plants selectively. That is, the leaves of *Nicotiana kawakamii* were eaten up almost completely, but 70% or more of the leaves were left in *Nicotiana umbratica*, and the F1 hybrid was almost in an undamaged state even after one day (the area of left leaves was 80% or more).

(4) Example 2-4

Figure 12:
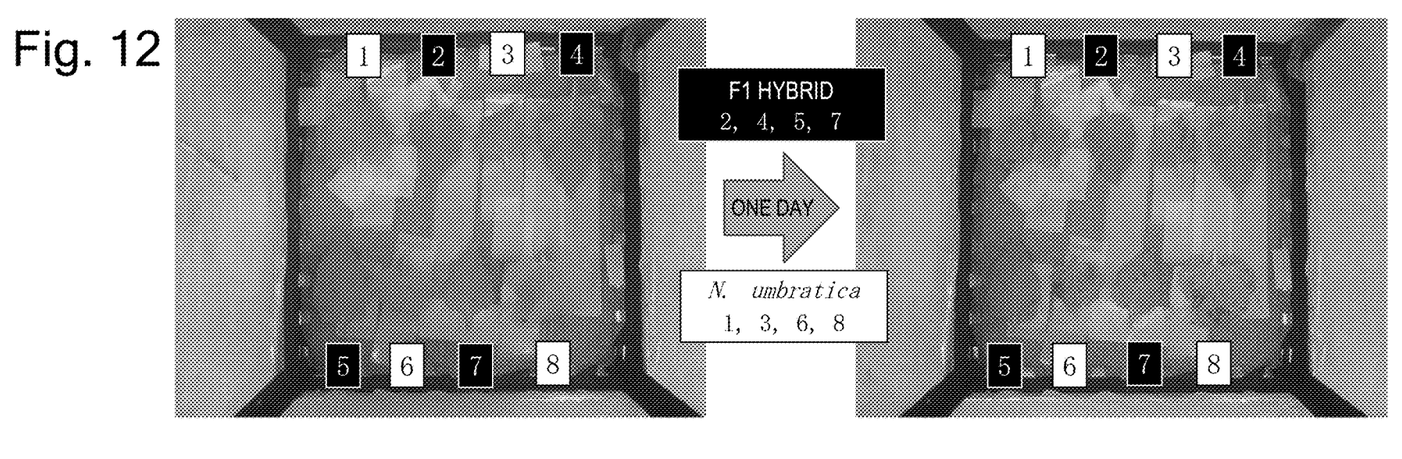
FIG. 12 includes a photograph (left) showing an arrangement of leaves of each plant of an F1 hybrid and *Nicotiana umbratica*, and a photograph (right) showing a state one day after larvae of oriental tobacco budworm (*Helicoverpa assulta*) are placed in an investigation on insect resistance against larvae of oriental tobacco budworm (*Helicoverpa assulta*) in Example 2-4.
Figure 13:
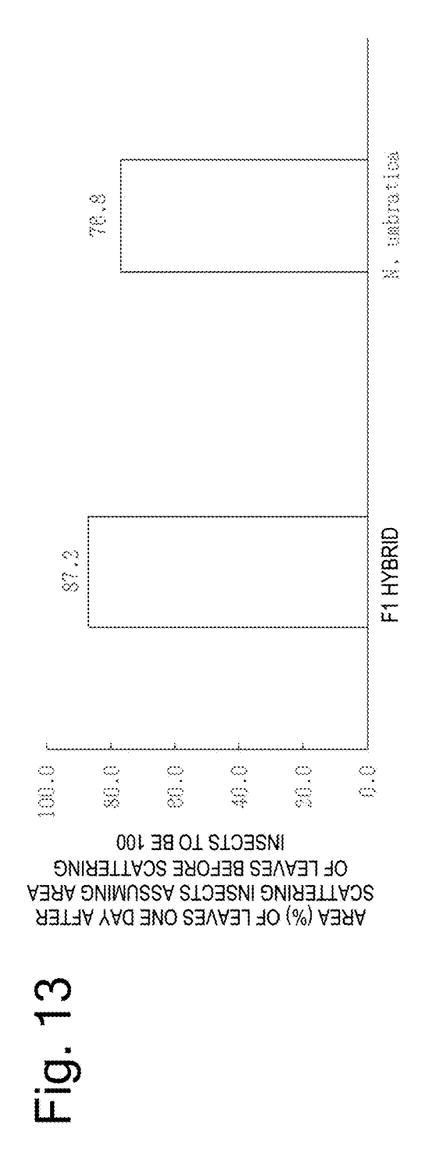
FIG. 13 is a bar graph showing a ratio (%) of an area of leaves after scattering insects to an area of leaves before scattering insects in Example 2-4.

In Example 2-2, leaves of *Nicotiana umbratica* as Comparative Example in addition to the F1 hybrid were arranged as shown in FIG. 12. The area (%) of leaves one day after scattering the insects assuming the area of leaves before scattering the insects to be 100 is shown in FIG. 13. The larvae of oriental tobacco budworm (*Helicoverpa assulta*) ate the leaves of respective plants selectively. That is, the F1 hybrid was almost in an undamaged state even after one day (the area of left leaves was 87.2%). *Nicotiana umbratica* was also not eaten so much, but was eaten significantly more than the F1 hybrid (the left area was 76.8%, which was lower than that of the F1 hybrid by 10% or more.).

As shown in Examples 2-1 to 2-4, it was made clear that the F1 hybrid of the present invention has remarkably stronger resistance against feeding damage by larvae of oriental tobacco budworm (*Helicoverpa assulta*) than *Nicotiana kawakamii*, and further, has significantly stronger resistance against feeding damage by larvae of oriental tobacco budworm (*Helicoverpa assulta*) than *Nicotiana umbratica*.

Example 3 Component Analysis of F1 Hybrid Between *Nicotiana umbratica* and *Nicotiana kawakamii*

In the present Example, component analysis of the F1 hybrid, F1, between *Nicotiana umbratica* and *Nicotiana kawakamii* was performed using GC/MS. As Comparative Example, *Nicotiana umbratica* was used.

Procedure

In a 50 mL centrifuge tube, 4 g of leaves just after being cut from a plant body are placed.

Hexane in a volume of 20 mL is added to perform extraction by shaking at 200 rpm for 60 minutes.

Contents in the centrifuge tube after shaking are filtrated with a filter paper, an appropriate amount of sodium sulfate is added to a filtrate, and a resultant mixture is left to stand for 30 minutes to perform dehydration.

The liquid after dehydration is filtrated again, and a resultant liquid is then sealed in a vial and used as an analysis sample to perform GC (gas chromatography).

The total ion chromatogram obtained is analyzed to make relative comparison of the amount of terpene compound A as an object component (RI (Retention index) 1617) (1-isopropyl-5-(hydroxymethyl)-8-methyltricyclo[4.4.0.02,8]dec-4-ene). It is to be noted that n-eicosane was used as an internal standard substance, and a ratio (ratio to internal standard substance) of the measured value in analyzing terpene compound A in each analysis sample to the measured value in analyzing n-eicosane was calculated to use as the amount of terpene compound A in each analysis sample.

Analysis Condition

Device: Agilent 5977 B series GC/MSD system (7980B GC/5977B MSD)

Column: HP-1MS (model number 19091S-733, length (m) 30×inner diameter (mm) 0.25×film thickness (µm) 1.00)

Temperature-increasing program: 40° C. for 1 minute, 40 to 200° C. at 5° C./min, 200 to 220° C. at 1° C./min, 220 to 300° C. at 5° C./min, 300° C. for 21 minutes Inlet: splitless, 1 µL, 300° C.

Detector: Scan mode (m/z 40 to 400)

Figure 14:
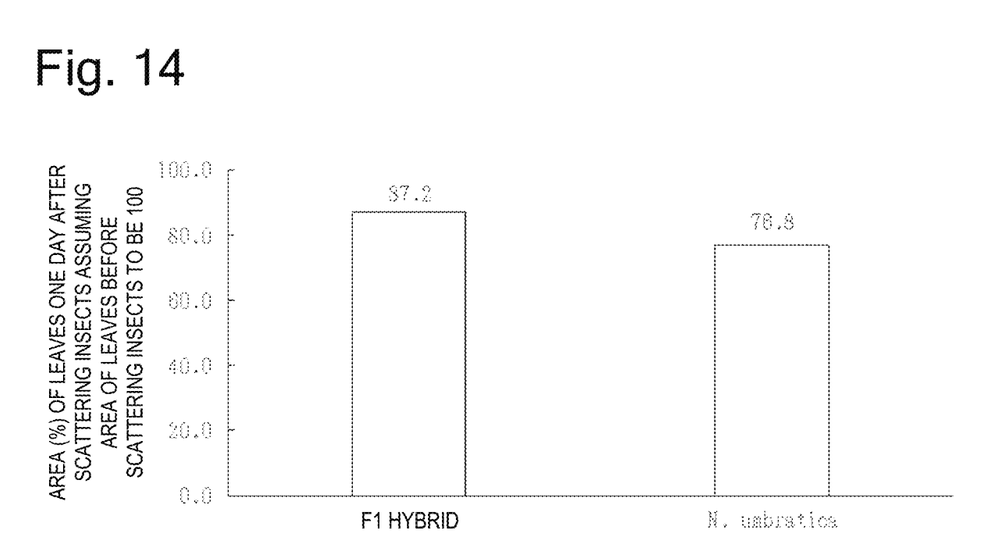
FIG. 14 is a bar graph showing an amount (ratio to internal standard substance) of terpene compound A in an F1 hybrid and *Nicotiana umbratica* in Example 3.

Terpene compound A (1-isopropyl-5-(hydroxymethyl)-8-methyltricyclo[4.4.0.02,8]dec-4-ene) is a component that contributes to a characteristic scent (preferred scent as tobacco) in *Nicotiana umbratica*. As a result of the component analysis, the amount (ratio to internal standard substance) of terpene compound A was 0.85 in *Nicotiana umbratica*, but was 0.98 in the F1 hybrid as shown in FIG. 14. Accordingly, it was ascertained that the component that contributes to the characteristic scent (preferred scent as tobacco) does not decrease in the F1 hybrid as compared to *Nicotiana umbratica*.

The invention claimed is:

1. An F1 hybrid plant between *Nicotiana umbratica* and *Nicotiana kawakamii*, or a portion thereof, said F1 hybrid plant having at least one of the characteristics selected from the group consisting of:
   a ratio (%) of height of a lowermost flower to grass height increases as compared to *Nicotiana umbratica;*
   a number of flowers per plant is smaller than that of *Nicotiana umbratica;* a leaf length or a leaf width of a largest leaf is longer than that of *Nicotiana umbratica*, or both of a leaf length and a leaf width of a largest leaf are longer than those of *Nicotiana umbratica*;

a number of branches decreases as compared to the number of branches of *Nicotiana umbratica*;

a yield of an above-ground part increases as compared to *Nicotiana umbratica*;

a yield of dried leaves increases as compared to *Nicotiana umbratica*;

insect resistance against a defoliator pest is improved as compared to *Nicotiana kawakamii*;

insect resistance against a defoliator pest is improved as compared to both of *Nicotiana kawakamii* and *Nicotiana umbratica*;

insect resistance against a stored-tobacco pest is improved as compared to *Nicotiana kawakamii*; and insect resistance against a stored-tobacco pest is improved as compared to both of *Nicotiana kawakamii* and *Nicotiana umbratica*.

2. The F1 hybrid plant or a portion thereof according to claim 1, wherein the portion is selected from the group consisting of a leaf, a stem, a root, a seed, a flower, pollen, an anther, an ovule, a pedicel, a meristematic tissue, a seed leaf, an embryonic axis, a pericycle, an embryo, an endosperm, an explant tip, a callus, a tissue-cultured product, a bud, a cell, and a protoplast.

3. The F1 hybrid plant or a portion thereof according to claim 1, wherein a seed parent is *Nicotiana umbratica*, and a pollen parent is *Nicotiana kawakamii*.

4. The F1 hybrid plant or a portion thereof according to claim 1, wherein a pollen parent is *Nicotiana umbratica*, and a seed parent is *Nicotiana kawakamii*.

5. The F1 hybrid plant or a portion thereof according to claim 1, wherein a ratio (%) of height of a lowermost flower to grass height increases as compared to *Nicotiana umbratica*.

6. The F1 hybrid plant or a portion thereof according to claim 1, wherein a number of flowers per plant is smaller than that of *Nicotiana umbratica*.

7. The F1 hybrid plant or a portion thereof according to claim 1, wherein a leaf length or a leaf width of a largest leaf is longer than that of *Nicotiana umbratica*, or both of a leaf length and a leaf width of a largest leaf are longer than those of *Nicotiana umbratica*.

8. The F1 hybrid plant or a portion thereof according to claim 1, wherein a number of branches decreases as compared to the number of branches of *Nicotiana umbratica*.

9. The F1 hybrid plant or a portion thereof according to claim 1, wherein a yield of an above-ground part increases as compared to *Nicotiana umbratica*.

10. The F1 hybrid plant or a portion thereof according to claim 1, wherein a yield of dried leaves increases as compared to *Nicotiana umbratica*.

11. The F1 hybrid plant or a portion thereof according to claim 1, wherein insect resistance against a defoliator pest is improved as compared to *Nicotiana kawakamii*.

12. The F1 hybrid plant or a portion thereof according to claim 1, wherein insect resistance against a defoliator pest is improved as compared to both of *Nicotiana kawakamii* and *Nicotiana umbratica*.

13. The F1 hybrid plant or a portion thereof according to claim 1, wherein insect resistance against a stored-tobacco pest is improved as compared to *Nicotiana kawakamii*.

14. The F1 hybrid plant or a portion thereof according to claim 1, wherein insect resistance against a stored-tobacco pest is improved as compared to both of *Nicotiana kawakamii* and *Nicotiana umbratica*.

15. The F1 hybrid plant or a portion thereof according to claim 11, wherein the defoliator pest is selected from the group consisting of oriental tobacco budworm (*Helicoverpa assulta*), tobacco budworm (*Heliothis virescens*), cotton bollworm (*Helicoverpa armigera*), tobacco hornworm (*Manduca sexta*), *Spodoptera litura*, and *Spodoptera exigua*.

16. A method for making an F1 hybrid plant, comprising hybridizing *Nicotiana umbratica* and *Nicotiana kawakamii* and choosing the F1 hybrid plant having at least one of the characteristics selected from the group consisting of:

a ratio of a height of a lowermost flower to a grass height increased as compared to *Nicotiana umbratica* after hybridizing *Nicotiana umbratica* and *Nicotiana kawakamii*;

a number of flowers per plant smaller than the number of flowers of *Nicotiana umbratica* after hybridizing *Nicotiana umbratica* and *Nicotiana Kawakamii*, a longer leaf length or a leaf width of a largest leaf or both of a longer leaf length and a leaf width of a largest leaf than *Nicotiana umbratica* after hybridizing *Nicotiana umbratica* and *Nicotiana kawakamii*;

a number of branches decreased as compared to *Nicotiana umbratica* after hybridizing *Nicotiana umbratica* and *Nicotiana kawakamii*;

a yield of an above-ground part increased as compared to *Nicotiana umbratica* after hybridizing *Nicotiana umbratica* and *Nicotiana kawakamii*; and a yield of dried leaves increased as compared to *Nicotiana umbratica* after hybridizing *Nicotiana umbratica* and *Nicotiana Kawakamii*.

17. The method according to claim 16, wherein a seed parent is *Nicotiana umbratica*, and a pollen parent is *Nicotiana kawakamii*.

18. The method according to claim 16, wherein a pollen parent is *Nicotiana umbratica*, and a seed parent is *Nicotiana kawakamii*.

19. The method according to claim 16, further comprising a step of choosing the F1 hybrid plant having a ratio (%) of a height of a lowermost flower to a grass height increased as compared to *Nicotiana umbratica* after hybridizing *Nicotiana umbratica* and *Nicotiana kawakamii*.

20. The method according to claim 16, further comprising a step of choosing the F1 hybrid plant having a number of flowers per plant smaller than the number of flowers of *Nicotiana umbratica* after hybridizing *Nicotiana umbratica* and *Nicotiana Kawakamii*.

21. The method according to claim 16, further comprising a step of choosing the F1 hybrid plant having a longer leaf length or a leaf width of a largest leaf, or both of a longer leaf length and a leaf width of a largest leaf than *Nicotiana umbratica* after hybridizing *Nicotiana umbratica* and *Nicotiana kawakamii*.

22. The method according to claim 16, further comprising a step of choosing the F1 hybrid plant having a number of branches decreased as compared to *Nicotiana umbratica* after hybridizing *Nicotiana umbratica* and *Nicotiana Kawakamii*.

23. The method according to claim 16, further comprising a step of choosing the F1 hybrid plant having a yield of an above-ground part increased as compared to *Nicotiana umbratica* after hybridizing *Nicotiana umbratica* and *Nicotiana kawakamii*.

24. The method according to claim 16, further comprising a step of choosing the F1 hybrid plant having a yield of dried leaves increased as compared to *Nicotiana umbratica* after hybridizing *Nicotiana umbratica* and *Nicotiana Kawakamii.*

25. A composition comprising the F1 hybrid plant or a portion thereof according to claim 1.

26. The composition according to claim 25, being in a cut tiller, powder, sheet, or solution form.

27. A product comprising the F1 hybrid plant or a portion thereof according to claim 1.

28. A product comprising the composition according to claim 25.

29. The product according to claim 27, selected from the group consisting of a tobacco product, a perfume, an agricultural chemical, and a pharmaceutical product.

30. A method for making an extract of an F1 hybrid plant which comprises extracting a product from the F1 hybrid plant according to claim 1.

31. The method according to claim 30, which comprises:
   cutting, grinding, or pulverizing the F1 hybrid plant according to claim 1 or a portion thereof to produce a composition; and
   subjecting said composition to extraction to produce said product.

\* \* \* \* \*